(12) United States Patent
Rao et al.

(10) Patent No.: US 10,234,409 B2
(45) Date of Patent: Mar. 19, 2019

(54) TEST EQUIPMENT ARRANGEMENT HAVING A SUPERHEAT CONTROLLER

(71) Applicant: DunAn Microstaq, Inc., Austin, TX (US)

(72) Inventors: Arvind Rao, Austin, TX (US); Chen Yang, Austin, TX (US); Jennifer O'Keefe, Austin, TX (US); Buu Chung, Buda, TX (US)

(73) Assignee: DunAn Microstaq, Inc., Austin, TX (US)

( * ) Notice: Subject to any disclaimer, the term of this patent is extended or adjusted under 35 U.S.C. 154(b) by 153 days.

(21) Appl. No.: 15/265,798

(22) Filed: Sep. 14, 2016

(65) Prior Publication Data
US 2017/0082336 A1    Mar. 23, 2017

Related U.S. Application Data

(60) Provisional application No. 62/219,841, filed on Sep. 17, 2015.

(51) Int. Cl.
*F25B 49/02* (2006.01)
*G01N 25/00* (2006.01)
*G01M 99/00* (2011.01)

(52) U.S. Cl.
CPC .......... *G01N 25/00* (2013.01); *G01M 99/008* (2013.01)

(58) Field of Classification Search
CPC ........ F25B 2341/065; F25B 2400/0411; F25B 2600/25; F25B 2600/2517; F25B 41/003; F25B 41/04; F25B 41/062; F25B 2333/001; F25B 2700/00; G01N 25/00; G01M 99/008; G01K 2013/026

USPC .......................... 374/1, 141, 143; 324/756.01
See application file for complete search history.

(56) References Cited

U.S. PATENT DOCUMENTS

| | | | | |
|---|---|---|---|---|
| 5,820,262 A * | 10/1998 | Lechner | ................ | F25B 49/005 374/45 |
| 7,392,396 B2 * | 6/2008 | Fernando | ................ | G06F 21/83 380/44 |
| 8,813,498 B2 * | 8/2014 | Kopecek | .................. | F01K 25/10 415/1 |
| 9,140,613 B2 | 9/2015 | Arunasalam et al. | | |
| 2003/0208333 A1 * | 11/2003 | Starling | .................. | G01K 13/12 702/135 |
| 2007/0186620 A1 * | 8/2007 | Kurtz | .................... | G01L 23/221 73/35.12 |
| 2011/0289948 A1 * | 12/2011 | Thybo | ....................... | F25B 5/02 62/115 |
| 2011/0313588 A1 * | 12/2011 | Jensen | ....................... | H02J 3/14 700/296 |
| 2015/0059373 A1 * | 3/2015 | Maiello | ................. | F25B 49/022 62/115 |
| 2015/0068231 A1 * | 3/2015 | Rite | ........................ | F25B 49/02 62/115 |
| 2015/0362236 A1 * | 12/2015 | Jiang | ..................... | F25B 41/062 137/12 |

(Continued)

FOREIGN PATENT DOCUMENTS

JP      2006284074 A  * 10/2006

*Primary Examiner* — Gail Kaplan Verbitsky
(74) *Attorney, Agent, or Firm* — MacMillan, Sobanski & Todd, LLC

(57) ABSTRACT

A test equipment arrangement includes a superheat controller configured for connection to a unit under test, and further configured to test at least one operational parameter of the unit under test.

15 Claims, 4 Drawing Sheets

(56) References Cited

U.S. PATENT DOCUMENTS

2016/0200176 A1\* 7/2016 Stanke ................. B60H 1/3211
                                                    62/115
2016/0320110 A1\* 11/2016 Ishida .................. F24F 2110/00
2017/0002932 A1\* 1/2017 Fuller ....................... F16K 1/46
2017/0038108 A1\* 2/2017 Mercer .................. F25B 49/02

\* cited by examiner

TEST EQUIPMENT ARRANGEMENT HAVING A SUPERHEAT CONTROLLER

CROSS-REFERENCE TO RELATED APPLICATIONS

This application claims the benefit of U.S. Provisional Application No. 62/219,841, filed Sep. 17, 2015, the disclosure of which is incorporated herein by reference.

BACKGROUND OF THE INVENTION

This invention relates in general to test equipment arrangements. In particular, this invention relates to an improved end of line test equipment arrangement having a superheat controller that is configured to replace certain components used in a conventional end of line test equipment arrangement.

U.S. Pat. No. 9,140,613 discloses a superheat controller (SHC). The SHC disclosed therein is a single, self-contained, stand-alone device which contains all the sensors, electronics, and processing capability to automatically detect a fluid type, such as refrigerant, and report the superheat of multiple common fluid types used in residential, industrial, and scientific applications. U.S. Pat. No. 9,140,613 is incorporated herein in its entirety.

FIGS. 3 and 4 herein illustrate a known SHC 10, which is similar to the superheat controller disclosed in U.S. Pat. No. 9,140,613. As shown in FIGS. 3 and 4, the illustrated embodiment of the SHC 10 includes a housing 12 having a body 14, a cover 16, and a fluid inlet member 18. The fluid inlet member 18 may be secured to the housing 12 by a mounting ring 19. The mounting ring 19 attaches the fluid inlet member 18 to the housing 12 portion by a threaded connection. Alternatively, the mounting ring 19 may be attached to the fluid inlet member 18 by any desired method, such as by welding or press fitting. In the embodiment illustrated in FIGS. 3 and 4, the fluid inlet member 18 is a brass fitting having a centrally formed opening that defines a sealing surface 20. When used in a known manner in a conventional heating, ventilating, air conditioning, and refrigeration (HVAC-R) system (not shown), the sealing surface 20 of the SHC 10 may engage a connector in the HVAC-R system to define a metal-to-metal seal.

Known superheat controllers include a pressure sensor as an integral component thereof. For example, the known SHC 10 includes an integrated pressure and temperature sensor 22 having pressure sensor portion 24 and a temperature sensor portion 26 mounted to a printed circuit board (PCB) 28. A superheat processor 30, a data-reporting or communication module 32, and an Input/Output (IO) module 34 are also mounted to the PCB 28. The IO module 34 is a physical hardware interface that accepts input power and reports data through available hard-wired interfaces, such as wires or cables 36, to the superheat processor 30. Target devices that may be connected to the SHC 10 via the IO module 34 are schematically illustrated at 38 in FIG. 4 and may include additional temperature sensors, laptop and notebook computers, cell phones, memory cards, and other devices. Alternatively, the target devices 38 may be connected to the communication module 32 by a wireless connection.

The superheat processor 30 is mounted to the PCB 28 and is a high-resolution, high accuracy device that processes the input signals from the pressure and temperature sensor portions 24 and 26, respectively, of the integrated pressure and temperature sensor 22, detects the fluid type, calculates the superheat of the fluid, and provides an output that identifies the level of the calculated superheat. The superheat processor 30 may also be configured to provide other data, such as fluid temperature, fluid pressure, fluid type, relevant historical dates maintained in an onboard memory (such as alarm and on-off history), and other desired information. Advantageously, the superheat processor 30 maintains a high level of accuracy over a typical operating range of pressure and temperature after a one-time calibration. Non-limiting examples of suitable superheat processors include microcontrollers, Field Programmable Gate Arrays (FPGAs), and Application Specific Integrated Circuits (ASICs) with embedded and/or off-board memory and peripherals.

Conventional end of line test equipment arrangements may be used to test devices such as microvalves, microvalve enabled devices, other electronic fluid valves, and other electronic devices such as pressure sensors and flow sensors after the devices have been manufactured and/or assembled. The conventional end of line test equipment arrangement may include a test stand with one or more of the following test components configured to test at least one operational parameter of a device or unit under test (UUT): a multimeter (to identify and measure input voltage to the UUT), a thermistor, a pressure transducer (to measure input pressure to the device), a pulse width modulation (PWM) driver (to control power to the device), a pressure regulator, a pressure reducer, one or more power sources of electrical power, a computer, and a data acquisition device.

There remains, however, a need in the art for a simplified end of line test equipment arrangement that has fewer test components and is therefore easier to construct and is more efficient.

SUMMARY OF THE INVENTION

The present application describes various embodiments of an improved test equipment arrangement wherein certain test components used in the test equipment arrangement are replaced with a superheat controller.

In one embodiment, a test equipment arrangement includes a superheat controller configured for connection to a unit under test, and further configured to test at least one operational parameter of the unit under test.

In another embodiment, the test equipment arrangement includes a test component configured for connection to a unit under test, and further configured to test at least one operational parameter of the unit under test. A superheat controller is configured for connection to the unit under test, and also configured to test at least one operational parameter of the unit under test not tested by the test component. The superheat controller includes a processer configured to perform at least one of the functions of a multimeter, a pulse width modulation driver, and a pressure transducer.

In an additional embodiment, a method of testing an electronic device includes connecting a superheat controller to the electronic device, wherein the superheat controller is configured to test at least one operational parameter of the electronic device. The at least one operational parameter of the electronic device is then tested with the superheat controller.

Various advantages of the invention will become apparent to those skilled in the art from the following detailed description, when read in view of the accompanying drawings.

DETAILED DESCRIPTION OF THE PREFERRED EMBODIMENTS

Figure 1:
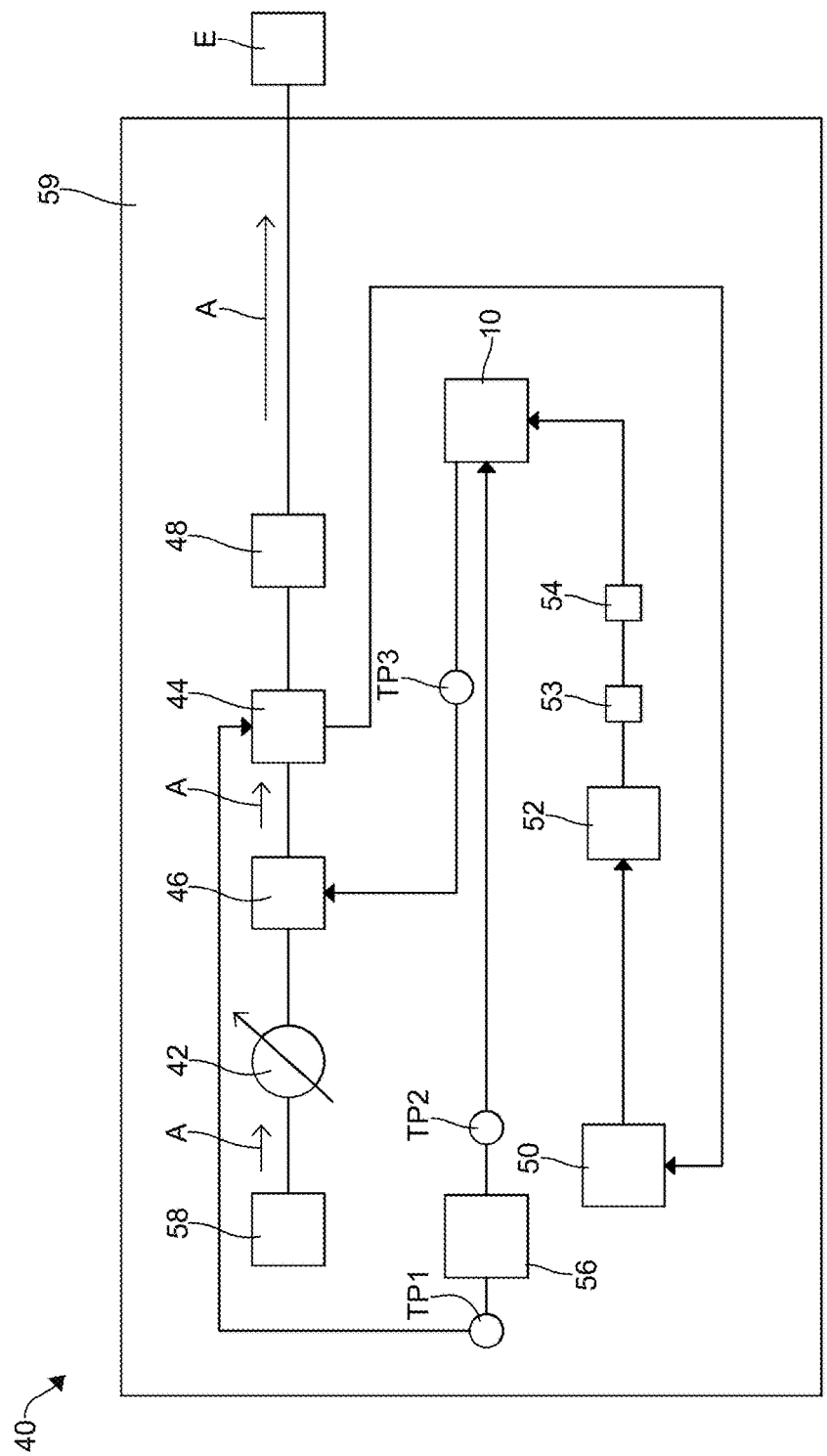
FIG. 1 is a block diagram illustrating a first embodiment of an improved end of line test equipment arrangement according to this invention.

Referring now to FIG. 1, a first embodiment of an improved test equipment arrangement according to the invention is shown generally at 40.

The test equipment arrangement 40 may be an end of line test equipment arrangement and thus configured to test devices, such as a unit under test (UUT) 46, after the UUT 46 has been manufactured and/or assembled. Alternatively, the test equipment arrangement 40 may be configured to test a UUT 46 at any stage of its manufacture and/or assembly. The improved test equipment arrangement 40 includes a pressure regulator 42, a pressure sensor or transducer 44, and a unit under test (UUT) 46 located between the pressure regulator 42 and the pressure transducer 44. The pressure transducer 44 measures input pressure to the UUT 46. Pressure data from the pressure transducer 44 may be routed through a data acquisition device 50, a processor, such as a computer 52, and a converter module 54 connected to the SHC 10. A pressure reducer 48 may be connected to the pressure transducer 44.

The pressure reducer 48 may be any desired pressure reducer, including a conventional pressure reducer configured to delay pressurized gas moving through the UUT 46 from going to ambient air pressure. The pressure transducer 44 may be any desired pressure transducer, such as a Viatran model 247 pressure transducer, or any pressure transducer configured to convert pressure into an electrical signal. The converter module 54 may be any desired converter module, such as a U485G converter module, or any converter module configured to facilitate communication conversion from USB to RS485 or RS422 data protocols.

The computer 52 may have a USB hub 53 attached thereto for connecting one or more SHCs 10 within the test equipment arrangement 40. The SHC 10 may be further connected to the UUT 46. The SHC 10, as well as any of the other test components of the test equipment arrangement 40, may be powered by a power supply 56. In the illustrated embodiment, pressurized gas, such as nitrogen or air from a source of pressurized gas 58, may be introduced to the UUT 46 through the pressure regulator 42 in a known manner. The pressurized gas travels from the pressure regulator 42, in the direction of the arrows A, through the UUT 46, the pressure transducer 44, the pressure reducer 48, and may be vented into the environment E in which the test equipment arrangement 40 is located.

As used herein, the following terms and phrases are defined as indicated:

1. "Unit Under Test" (UUT): a device that needs power to be actuated or to perform a desired task. The UUT 46 may include devices such as modular silicon expansion valves (MSEVs), other microvalve enabled devices, microvalves, other electronic fluid valves, and other electronic devices such as pressure sensors and flow sensors.

2. "Modular Silicon Expansion Valve" (MSEV): an electronically controlled, normally closed, and single flow directional refrigerant expansion valve. The MSEV may be used for refrigerant mass flow control in heating, ventilating, and air conditioning and refrigeration (HVAC-R) applications. The MSEV provides precise superheat control and includes a microvalve embedded therein. One example of a suitable MSEV is the MSEV manufactured by DunAn Microstaq, Inc. of Austin, Tex.

3. "Pulse Width Modulation" (PWM): a modulation technique used to encode a message into a pulsing signal. PWM is typically used to allow the control of the power supplied to electrical devices.

4. PWM driver: a device that controls the power to the UUT. An average value of voltage and current fed to the UUT may be controlled by turning the power from a source of power to the electrical device on and off at a fast rate. For power delivery, PWM may be used to control the amount of power delivered to a load, such as the UUT, without incurring the losses that would result from linear power delivery by resistive means. In addition to power delivery, the PWM driver may be useful in many other applications, including the control of servo-mechanisms, telecommunications signal modulation, voltage regulation, and for audio effects and amplification.

5. "Superheat Controller" (SHC): a device that contains all the sensors, electronics, and processing capability required to automatically detect multiple fluid types, such as refrigerants, with minimal need for re-calibration, and report the superheat of the multiple common fluid types used in residential, industrial, and scientific applications. One example of such a superheat controller is disclosed in U.S. Pat. No. 9,140,613. The SHC 10 disclosed herein may be configured to provide additional data, such as fluid temperature, fluid pressure, fluid type, historical dates maintained in an onboard memory (such as alarm and on-off history), and other desired information. The SHC 10 may also be configured as a high-resolution processor that is able to detect and process resistance and voltage information and control the output of electricity from a source of electrical power, such as a power supply, to the UUT 46, and is able to detect and control input PWM and output pressure.

6. "Thermistor": a type of resistor having a resistance that varies significantly with temperature, and/or has a resistance that varies more than standard resistors.

7. "Data Acquisition Device": a device that converts analog waveforms into digital values for processing by the SHC 10.

8. "Converter Module": a module or device that performs communication conversion between USB computer ports and conventional RS485 and RS422 data networks. One non-limiting example of a suitable converter module is a U485G converter module.

The pressure transducer 44 may be configured to sense and measure gas and/or fluid pressure in the UUT 46. For example, the pressure transducer 44 may generate a signal, typically an electrical signal, as a function of the pressure imposed thereon. The pressure transducer 44 may be further configured to sense and measure input and/or output pressure of the UUT 46. In addition to sensing and measuring input and/or output pressure of the UUT 46, the pressure transducer 44 may be useful in many applications, such as to indirectly measure variables including fluid or gas flow, flow speed, fluid level, and altitude.

In addition to the functions of the superheat processor disclosed in U.S. Pat. No. 9,140,613, the superheat processor 30 within the SHC 10 may be configured as a high-resolution processor that is able to detect and process resistance and voltage information and control the output of electricity from a source of electrical power, such as the power supply 56, to the UUT 46.

The various test and other components of the test equipment arrangement 40 may be mounted or positioned on a stand, schematically illustrated at 59, and may be configured to test a plurality of UUTs 46, such as MSEVs.

In the illustrated embodiment of the test equipment arrangement 40 shown in FIG. 1, the SHC 10 is advantageously configured to perform a PWM function and further configured to protect the UUT 46 from overvoltage. This capability of the SHC 10 thus allows the test equipment arrangement 40 to be assembled without a conventional PWM driver to control power to the UUT 46, and without a conventional multimeter to read input voltage to the UUT 46. This saves space, as both the conventional PWM driver and the conventional multimeter are significantly larger than the SHC 10.

In the illustrated embodiment for example, the superheat processor 20 within the SHC 10 may be configured to protect the UUT 46 by detecting electrical resistance at the UUT 46 before supplying power to the UUT 46, thus obviating the need for a conventional multimeter. In lieu of a conventional multimeter, the superheat processor 20 within the SHC 10 may be provided with an algorithm to sense the input voltage supplied to the UUT 46 within the test equipment arrangement 40, and further to quickly shut off power to the UUT 46 before the UUT 46 is damaged if an over-voltage condition is sensed, thus obviating the need for both the conventional PWM driver and the conventional multimeter.

The SHC 10 may also perform a very large number of PWM cycles on the UUT 46 and, thus, rigorously test the UUT 46 for wear and tear. For example, the SHC 10 may execute one million or more PWM cycles on the UUT 46.

Various physical test reference points may be assigned within the test equipment arrangement 40. In the embodiment of the test equipment arrangement 40 shown in FIG. 1, three test points are shown at TP1, TP2, and TP3. For example, test point TP1 may be used to confirm whether a desired voltage, such as 5 V, has been routed to the pressure transducer 44. Test point TP2 may be used to confirm whether a desired voltage, such a 12 V or 24 V, has been routed to the SHC 10. Test point TP3 may be used to confirm that the desired PWM signal in being sent to the UUT 46. It will be understood that the test equipment arrangement 40 may be configured with any desired of test points configured to check or confirm the function of any test component of the test equipment arrangement 40.

Figure 2:
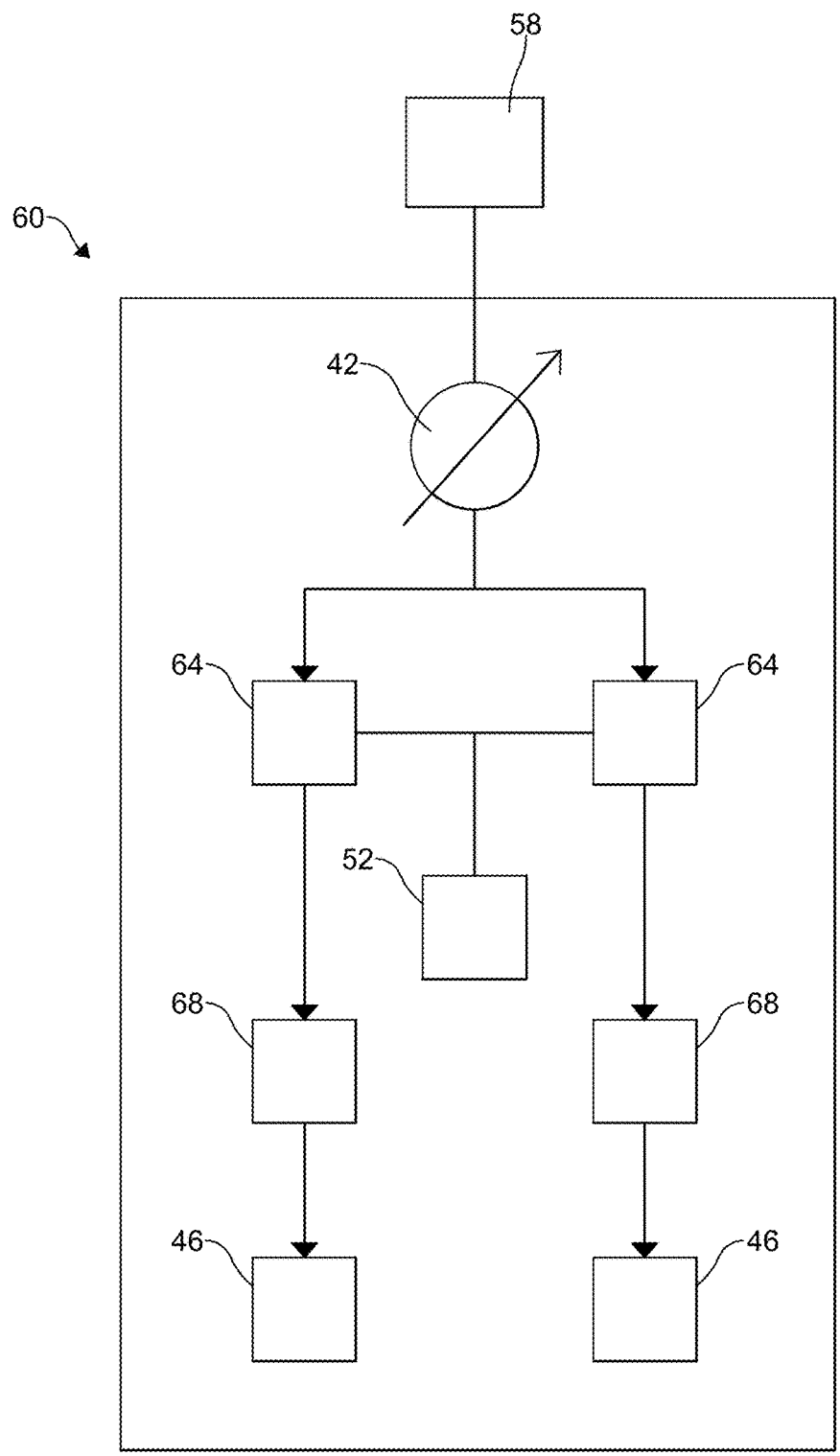
FIG. 2 is a block diagram illustrating a second embodiment of an improved end of line test equipment arrangement according to this invention.
Figure 3:
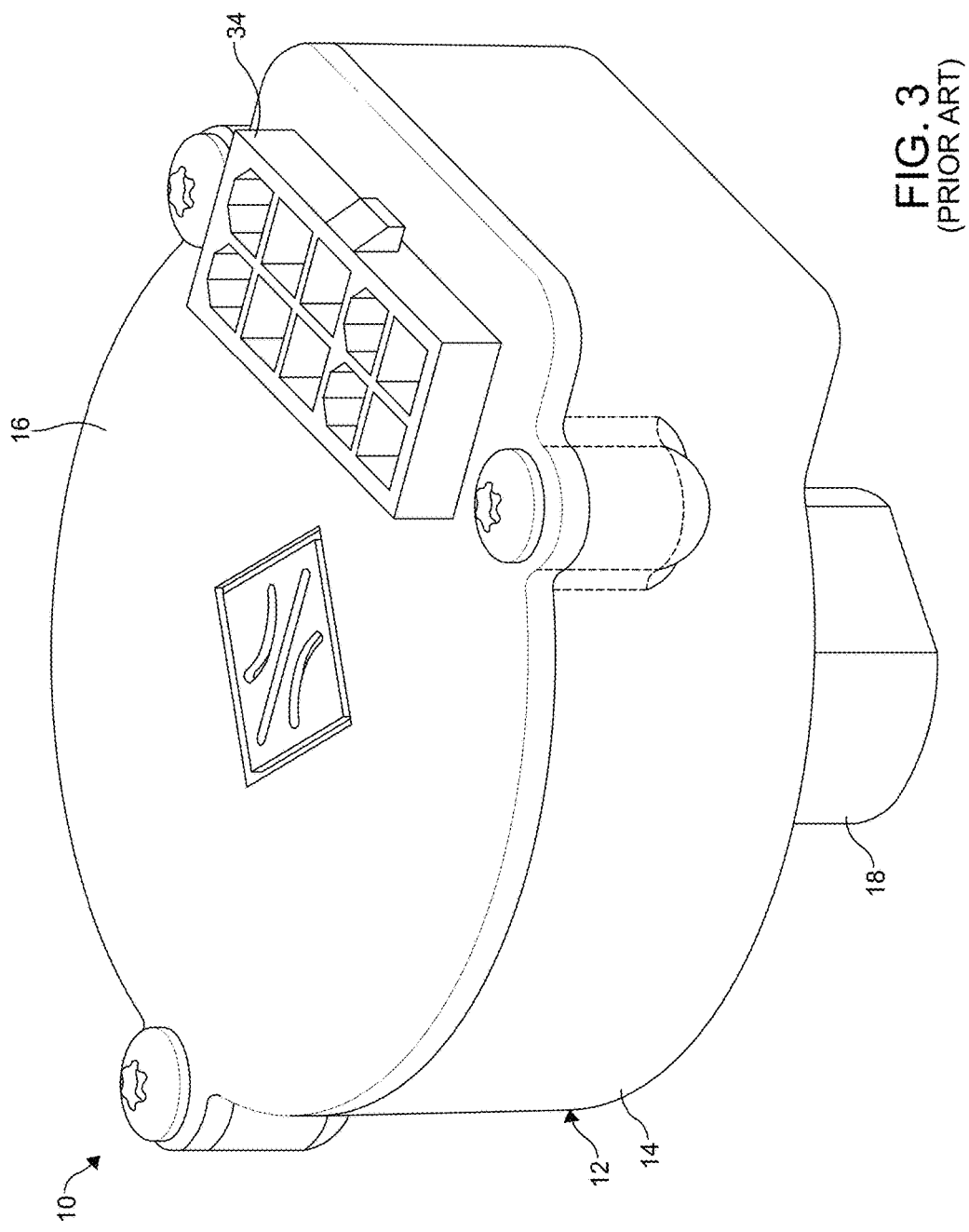
FIG. 3 is a perspective view of a known universal superheat controller.
Figure 4:
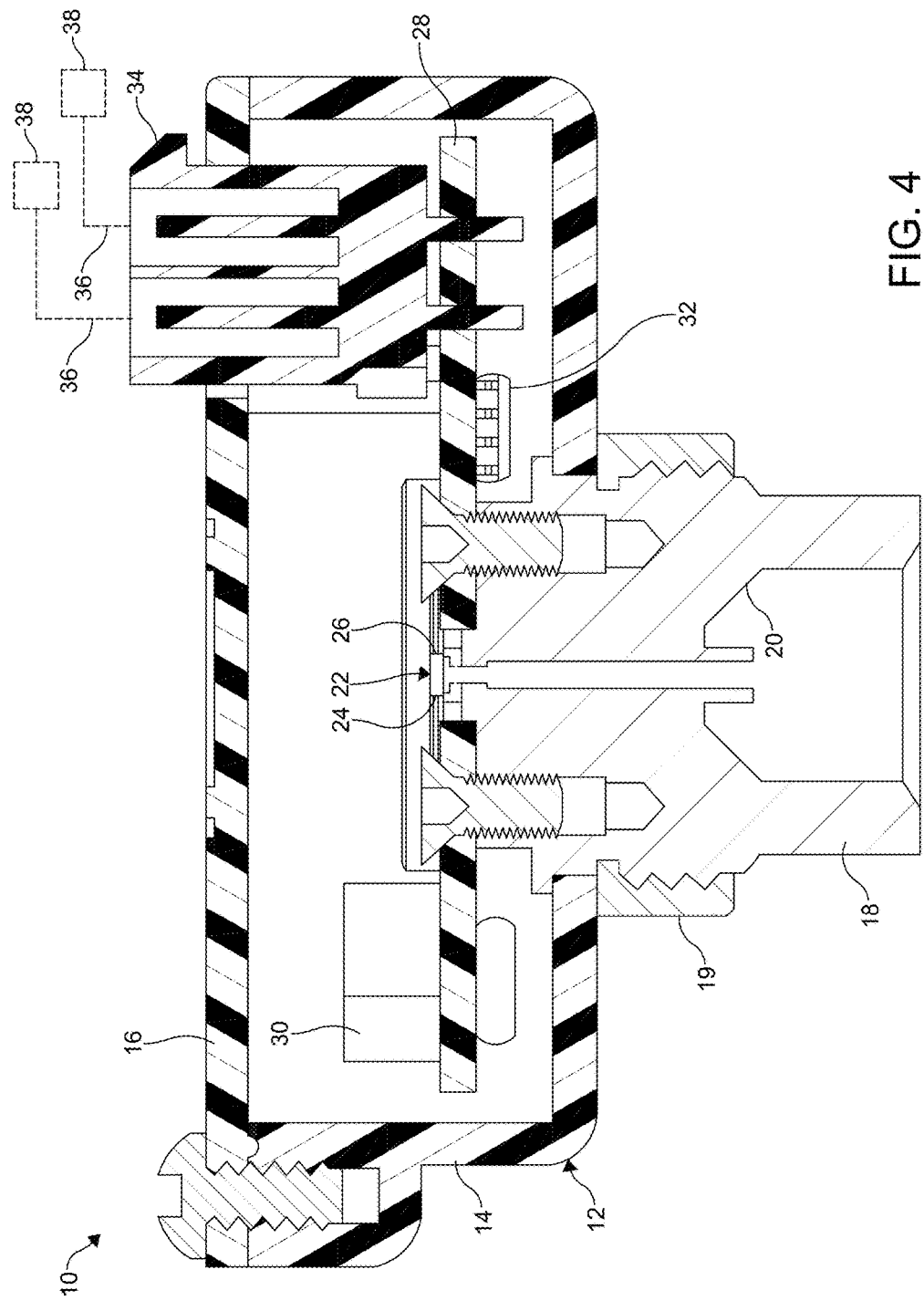
FIG. 4 is a cross sectional view of the known universal superheat controller illustrated in FIG. 3.

Referring now to FIG. 2, a second embodiment of an improved equipment arrangement according to the invention is shown generally at 60. Like the test equipment arrangement 40, the test equipment arrangement 60 may be an end of line test equipment arrangement and thus configured to test devices, such as a UUT 46, after the UUT 46 has been manufactured and/or assembled. Alternatively, the test equipment arrangement 60 may be configured to test a UUT 46 at any stage of its manufacture and/or assembly.

The illustrated improved test equipment arrangement 60 may be configured to test a plurality of the UUTs 46. Although two UUTs 46 are shown in FIG. 2, the line test equipment arrangement 60 may be configured to test any desired number of UUTs 46.

The improved test equipment arrangement 60 includes the pressure regulator 42 connected to each of two SHCs 64. Valves 68 are connected between each SHC 64 and the UUTs 46. The valves 68 control the flow of gas (i.e., turn the supply of gas on and off) to the UUTs 46. The valves 68 may be any desired type of valve, such as a solenoid valve. The SHCs 64 may be structurally identical to the SHC 10 illustrated in FIG. 1, but are advantageously configured to perform the functions of a conventional PWM driver, a conventional multimeter, and the pressure transducer 44. Like the test equipment arrangement 40, the UUTs 46 in the test equipment arrangement 60 are provided with pressurized gas, such as nitrogen or air that may be introduced to the UUTs 46 from the source of pressurized gas 58 and through the pressure regulator 42 in a known manner. The SHCs 64, as well as any of the test or other components of the test equipment arrangement 60, may be powered by one or more sources of electrical power, such as the power supply 56 (not shown in FIG. 2, but shown in FIG. 1). The various test components of the test equipment arrangement 60 may be mounted or positioned on a stand (not shown).

If desired, a data acquisition device, such as the data acquisition device 50, may be provided to communicate or provide an interface between the solenoid valves 68 and the computer 52.

In the embodiment illustrated in FIG. 2, each SHC 64 may be advantageously configured to perform a PWM driver function, act as a pressure transducer, and further configured to protect the UUTs 46 from overvoltage in the same manner as a conventional multimeter. This capability of the SHC 64 thus allows the test equipment arrangement 60 to be assembled without a conventional PWM driver, without a pressure transducer 44, and without a conventional multimeter.

As described above, a single SHC, including the SHCs 10 and 64, may replace one or more of the typical test components of a conventional end of line test equipment arrangement, such as the PWM driver, the multimeter, and the pressure transducer 44. Additionally, the SHCs 10 and 64 may be configured to perform the functions of other conventional end of line test equipment arrangement test components, such as a thermistor and any other desired test components. Thus, the use of the SHC 10 and the SHC 64 in lieu of any one or more of these end of line test equipment arrangement test components allows the improved end of line test equipment arrangements 40 and 60 to be simpler by reducing the number of test components used therein, and thereby reducing the size of the improved end of line test equipment arrangements 40 and 60. Further, the cost and the maintenance requirements of the improved end of line test equipment arrangements 40 and 60 relative to a conventional end of line test equipment arrangement may be reduced.

In FIGS. 1 and 2, the SHCs 10 and 64 are shown attached within the improved end of line test equipment arrangements 40 and 60, respectively. It will be understood however, that the SHCs 10 and 64 may be configured to: perform a PWM driver function, act as a pressure transducer, protect devices such as the UUTs 46 from overvoltage, or perform any combination of these functions, and may be used with any device upon which a PWM driver function, pressure sensing and measurement, and/or input voltage detection is desired. Such devices may include the MSEVs, described above, other microvalve enabled devices, microvalves, electronic fluid valves, and other electronic devices such as pressure sensors and flow sensors.

The principle and mode of operation of the invention have been described in its preferred embodiments. However, it should be noted that the invention described herein may be practiced otherwise than as specifically illustrated and described without departing from its scope.

What is claimed is:

1. An end of line test equipment arrangement comprising a superheat controller having a processor, a temperature sensor, and a pressure sensor therein, removably connectable to a unit under test, and operable to test at least one operational parameter of the unit under test;

wherein the unit under test is one of a modular silicon expansion valve, a microvalve enabled device, a microvalve, an electronic fluid valve, a pressure sensor, and a flow sensor;

wherein the superheat controller processor is provided with an algorithm that at least one of:

detects and processes electrical resistance and input voltage of the unit under test and controls an output of electricity from a source of electrical power to the unit under test, thus performing the function of a multimeter and protecting the unit under test from overvoltage;

provides a pulse width modulation (PWM) signal and controls the amount of power delivered to the unit under test, thus performing the function of a pulse width modulation driver;

measures input pressure to the unit under test, thus performing the function of a pressure transducer;

measures input temperature to the unit under test, thus performing the function of a thermistor; and presents test data output to an operator.

2. The end of line test equipment arrangement according to claim 1, wherein the unit under test is a modular silicon expansion valve.

3. The end of line test equipment arrangement according to claim 1, further including at least one test component operably connected to the unit under test.

4. The end of line test equipment arrangement according to claim 3, wherein the at least one test component is one or more of a multimeter, a thermistor, a pressure transducer, a pulse width modulation driver, a pressure regulator, and a pressure reducer.

5. The end of line test equipment arrangement according to claim 1, further including a computer connected to the superheat controller and the unit under test.

6. The end of line test equipment arrangement according to claim 5, further including a data acquisition device connected to the superheat controller and the unit under test.

7. The end of line test equipment arrangement according to claim 5, wherein the test data output is presented to the operator via the computer.

8. An end of the line test equipment arrangement comprising:

a test component operably connected to a unit under test; and a superheat controller connected to the unit under test and having a processor, a temperature sensor, and a pressure sensor therein;

wherein the superheat controller processor is provided with an algorithm that at least one of:

detects and processes electrical resistance and input voltage of the unit under test and controls an output of electricity from a source of electrical power to the unit under test, thus performing the function of a multimeter and protecting the unit under test from overvoltage;

provides a pulse width modulation (PWM) signal and controls the amount of power delivered to the unit under test, thus performing the function of a pulse width modulation driver;

measures input pressure to the unit under test, thus performing the function of a pressure transducer; and measures input temperature to the unit under test, thus performing the function of a thermistor; and presents test data output to an operator.

9. The end of line test equipment arrangement according to claim 8, wherein the test component is one or more of a multimeter, a thermistor, a pressure transducer, a pulse width modulation driver, a pressure regulator, and a pressure reducer.

10. The end of line test equipment arrangement according to claim 8, further including a computer connected to the superheat controller and the unit under test.

11. The end of line test equipment arrangement according to claim 10, wherein the test data output is presented to the operator via the computer.

12. A method of testing an electronic device comprising:

connecting a superheat controller to an electronic device, the superheat controller having a processor, a temperature sensor, and a pressure sensor therein, the processor provided with an algorithm; and using the algorithm to at least one of:

detect and process electrical resistance and input voltage of the unit under test and controls an output of electricity from a source of electrical power to the unit under test, thus performing the function of a multimeter and protecting the unit under test from overvoltage;

provide a pulse width modulation signal and control the amount of power delivered to the unit under test, thus performing the function of a pulse width modulation driver;

measure input pressure to the unit under test, thus performing the function of a pressure transducer;

measure input temperature to the unit under test, thus performing the function of a thermistor; and present test data output to an operator.

13. The method according to claim 12, wherein the electronic device is one of a modular silicon expansion valve, a microvalve enabled device, a microvalve, an electronic fluid valve, a pressure sensor, and a flow sensor.

14. The method according to claim 12, further including connecting the superheat controller and the electronic device within an end of line test equipment arrangement having at least one of a multimeter, a thermistor, a pressure transducer, a pulse width modulation driver, a pressure regulator, and a pressure reducer.

15. The method according to claim 12, wherein the test data output is presented to the operator via a computer.

* * * * *